United States Patent [19]

Hargrave et al.

[11] Patent Number: 5,087,625
[45] Date of Patent: Feb. 11, 1992

[54] PYRIDODIAZEPINES AND THEIR USE IN THE PREVENTION OR TREATMENT OF HIV INFECTION

[75] Inventors: Karl D. Hargrave, Brookfield, Conn.; Gunther Schmidt, deceased, late of Munich, Fed. Rep. of Germany, by his legal representative Margaret Schmidt; Wolfhard Engel; Vokhard Austel, both of Biberach an Der Riss, Fed. Rep. of Germany

[73] Assignees: Boehringer Ingelheim Pharmaceuticals, Inc., Ridgefield, Conn.; Dr. Karl Thomae GmbH, Biberach an der Riss, Fed. Rep. of Germany

[21] Appl. No.: 650,141

[22] Filed: Feb. 4, 1991

Related U.S. Application Data

[63] Continuation-in-part of Ser. No. 600,554, Oct. 19, 1990, which is a continuation-in-part of Ser. No. 438,922, Nov. 17, 1989, abandoned, which is a continuation-in-part of Ser. No. 372,728, Jun. 28, 1989, abandoned, which is a continuation-in-part of Ser. No. 340,937, Apr. 20, 1989, abandoned.

[51] Int. Cl.$^5$ ............... A61K 31/55; C07D 471/04; C07D 495/14
[52] U.S. Cl. ............... 514/220; 540/495; 540/557
[58] Field of Search .................. 514/220

[56] References Cited

U.S. PATENT DOCUMENTS 3,539,554 11/1970 Schmidt .................. 540/495

Primary Examiner—Robert Gerstl
Attorney, Agent, or Firm—David E. Frankhouser; Alan R. Stempel; Mary-Ellen M. Timbers

[57] ABSTRACT

Disclosed are novel pyridodiazepines. These compounds, as well as certain known 5,11-dihydro-6H-pyrido[2,3-b][1,4]benzodiazepin-6-ones are useful in the treatment of AIDS, ARC and related disorders associated with HIV infection.

3 Claims, No Drawings

PYRIDODIAZEPINES AND THEIR USE IN THE PREVENTION OR TREATMENT OF HIV INFECTION

RELATED APPLICATIONS

This is a continuation-in-part of application Ser. No. 600,554, filed Oct. 19, 1990, which is a continuation-in-part of application Ser. No. 438,922, filed Nov. 17, 1989, now abandoned, which is a continuation-in-part of application Ser. No. 372,728, filed June 28, 1989, now abandoned, which is a continuation-in-part of application Ser. No. 340,937, filed Apr. 20, 1989, now abandoned.

FIELD OF THE INVENTION

The invention relates to novel pyridodiazepines, methods for preparing these compounds, the use of these and related but known compounds in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins.

The conversion of the RNA to DNA is accomplished through the use of the enzyme reverse transcriptase (RT), which is included within the infecting virion along with the RNA. Reverse transcriptase has three enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Next, acting as a ribonuclease, RT frees the DNA just produced from the original viral RNA and then destroys the original RNA. Finally, acting as a DNA-dependent DNA polymerase, RT makes a second, complementary, DNA strand, using the first DNA strand as a template. The two strands form double-stranded DNA, the form of DNA found in the host cell's genome, which is integrated into the host cell's genome by another enzyme, called an integrase.

Compounds which inhibit the enzymatic functions of HIV-1 reverse transcriptase will inhibit replication of HIV-1 in infected cells. Such compounds are useful in the prevention or treatment of HIV-1 infection in human subjects.

SUMMARY OF THE INVENTION

A first aspect of the invention comprises a method for preventing or treating HIV-1 infection which comprises administering, to a human exposed to or infected by HIV-1, a prophylactically or therapeutically effective amount of certain pyridodiazepines. Some of these compounds are novel and some are known. All possess inhibitory activity against HIV-1 RT. A second aspect of the invention comprises novel pyridodiazepines. A third aspect of the invention comprises methods for making these novel compounds. A final aspect of the invention comprises pharmaceutical compositions suitable for the prevention or treatment of HIV-1 infection comprising the above mentioned compounds, both novel and known.

DETAILED DESCRIPTION OF THE INVENTION

A first aspect of the invention comprises a method for preventing or treating HIV-1 infection which comprises administering to a human, exposed to or infected by HIV-1, a prophylactically or therapeutically effective amount of a pyridodiazepine of the formula

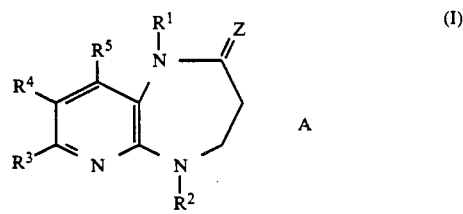

wherein,
A is a fused ring of the formula

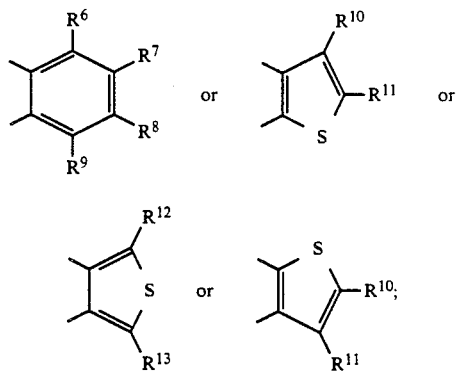

Z is oxygen, sulfur, =NCN or a group of the formula =NOR$^{14}$ wherein R$^{14}$ is alkyl of 1 to 3 carbon atoms;

R$^1$ is hydrogen, alkyl or fluoroalkyl of 1 to 4 carbon atoms, cyclopropyl, alkenyl or alkynyl of 3 to 4 carbon atoms, 2-halo-propen-1-yl, arylmethyl (wherein the aryl moiety is phenyl or thienyl, which is either unsubstituted or substituted by methyl, methoxy or halogen), acetyl, or alkoxyalkyl or alkylthioalkyl of 2 to 3 carbon atoms;

R$^2$ is alkyl or fluoroalkyl of 1 to 4 carbon atoms, cycloalkyl of 3 to 5 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, halogen or hydroxyl) or alkoxycarbonylmethyl wherein the alkoxy moiety contains 1 to 5 carbon atoms;

$R^3$, $R^4$ and $R^5$ are each independently hydrogen, alkyl of 1 to 3 carbon atoms or chloro, with the proviso that at least one of these substituents is hydrogen or methyl; or, one of $R^3$, $R^4$ and $R^5$ is butyl, alkanoyl of 2 to 4 carbon atoms, alkoxycarbonyl or 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, aryl or arylalkyl (wherein the alkyl moiety contains 1 to 3 carbon atoms, and the aryl moiety is phenyl, thienyl, furanyl, pyridyl, or imidazolyl, which is either unsubstituted or substituted by alkyl or alkoxy of 1 to 3 carbon atoms, hydroxyl or halogen), alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 3 carbon atoms, N-pyrrolidino, N-piperidino, N-morpholino, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, with the proviso that the remaining two substituents are hydrogen or methyl; or, when Z is oxygen, one of $R^3$, $R^4$ and $R^5$ is alkylsulfinyl or alkylsulfonyl of 1 to 3 carbon atoms, with the proviso that the remaining two substituents are hydrogen or methyl;

$R^6$, $R^7$, $R^8$ and $R^9$ are each hydrogen; or one of $R^6$, $R^7$, $R^8$ and $R^9$ is alkyl of 1 to 4 carbon atoms, alkanoyl of 2 to 4 carbon atoms, alkoxycarbonyl of 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 2 carbon atoms, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, and the remaining three substituents are hydrogen or two of the remaining three substituents are hydrogen and one is methyl, ethyl, or halogen;

$R^{10}$ and $R^{11}$ are each independently hydrogen, alkyl of 1 to 3 carbon atoms or halogen; and, $R^{12}$ and $R^{13}$ are each independently hydrogen, methyl, ethyl, or halogen.

In a subgeneric aspect, the invention comprises the above-described method wherein, in the compound of formula Ia,

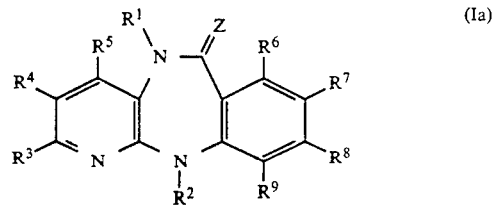

Z is oxygen or sulfur;

$R^1$ is hydrogen, alkyl of 1 to 3 carbon atoms, allyl, propargyl, 2-halo-propen-1-yl, methoxymethyl or methylthiomethyl;

$R^2$ is alkyl 1 to 4 carbon atoms, cycloalkyl of 3 to 4 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 4 carbon atoms;

$R^3$, $R^4$, and $R^5$ are each independently hydrogen, methyl, chloro, mono- or di-alkylamino wherein each alkyl moiety contains 1 to 3 carbon atoms, N-pyrrolidino, N-piperidino or N-morpholino, with the proviso that at least one of these substituents is hydrogen or methyl, or $R^5$ is ethyl, propyl or butyl with the remaining two substituents being hydrogen;

$R^6$ is hydrogen, or methyl or ethyl with the proviso that $R^7$ is hydrogen or methyl;

$R^7$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyloxy, alkanoylamino of 1 to 2 carbon atoms or cyano, with the proviso that $R^8$ is hydrogen;

$R^8$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyl, alkanoylamino of 1 to 2 carbon atoms or cyano, with the proviso that $R^7$ is hydrogen; or, $R^7$ and $R^8$ are both hydrogen, methyl or halogen; and, $R^9$ is hydrogen, or methyl with the proviso that $R^8$ is hydrogen or methyl.

In a further subgeneric aspect, the invention comprises the above described method wherein, in the compound of formula Ia, Z is oxygen or sulfur;

$R^1$ is hydrogen, 2-halo-2-propen-1-yl, or alkyl of 1 to 3 carbon atoms;

$R^2$ is alkyl of 1 to 4 carbon atoms or cycloalkyl of 3 to 4 carbon atoms;

$R^3$ is hydrogen, methyl, chloro, methoxy, mono- or di-alkylamino wherein each alkyl moiety contains 1 to 3 carbon atoms, or N-pyrrolidino;

$R^4$ and $R^5$ are each independently hydrogen or methyl; and, $R^6$ through $R^9$ are each hydrogen.

Compounds of formula I may, if desired, be converted into their non-toxic, pharmaceutically acceptable acid addition salts by conventional methods; for example, by dissolving a compound of formula I in a suitable solvent and acidifying the solution with one or more molar equivalents of the desired acid. The invention also comprises the use of such salts. Salt formation at any of $R^3$ through or $R^9$, when these are basic amines, is preferred.

Examples of inorganic and organic acids which may form non-toxic, pharmaceutically acceptable acid addition salts with a compound of formula I are the following: hydrochloric acid, hydrobromic acid, sulfuric acid, phosphoric acid, nitric acid, tartaric acid, citric acid, methanesulfonic acid and the like. Compounds of formula I usually form acid addition salts with one molar equivalent of the acid.

The above described compounds of formula I inhibit HIV-1 reverse transcriptase and thereby inhibit HIV-1 replication, making them useful in the method which constitutes the first aspect of the invention.

In carrying out this method, the compounds formula I may be administered in single or divided doses by the oral, parenteral or topical routes. A suitable oral dosage for such compounds would be in the range of about 10 to 500 mg per day. In parenteral formulations, a suitable dosage unit may contain from 1 to 50 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When such compounds are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkyleneglycols, petroleum jelly and the like. The pharmaceutical preparations can be prepared in a conventional manner and finished dosage forms can be solid dosage forms, for example, tablets, dragees, capsules, and the like, or liquid dosage forms, for example, solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers, such as polyethylene glycol.

For parenteral use, it is preferred to administer such compounds in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds can also be administered as solutions for nasal applications which may contain, in addition to the compounds, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinyl-pyrrolidone, polysorbates or glycerin. Microbial preservatives added may include benzalkonium chloride, thimerosal, chlorobutanol or phenylethyl alcohol.

Additionally, such compounds can be administered by suppository.

In its composition of matter aspect, the invention comprises novel compounds of formula I, wherein A and $R^1$ through $R^{13}$ are as set forth above and Z is sulfur, $=NCN$ and $=NOR^{12}$, and pharmaceutically acceptable acid addition salts thereof.

The invention also comprises the following novel compounds of formula I, wherein Z is oxygen, as well as the pharmaceutically acceptable acid addition salts thereof:

a) 5-(2-Chloro-2-propenyl)-5,11-dihydro-11-ethyl-6H-pyrido[2,3-b][1,4]benzodiazepin-6-one;

b) 5,11-Dihydro-2,5,8,11-tetramethyl-6H-pyrido[2,3-b][1,4]benzodiazepin-6-one;

c) 5,11-Diethyl-5,11-dihydro-10-methyl-6H-pyrido[2,3-b][1,4]benzodiazepin-6-one;

d) 5,8-Dimethyl-5,11-dihydro-11-ethyl-6H-pyrido[2,3-b][1,4]benzodiazepin-6-one;

e) 5,11-Dihydro-2,5,10,11-tetramethyl-6H-pyrido[2,3-b][1,4]benzodiazepin-6-one;

f) [5,11-Dihydro-6-oxo-6H-pyrido[2,3-b][1,4]benzodiazepin-11-yl]]acetic acid, tert-butylester;

g) 2-Chloro-5,11-dihydro-5-ethyl-11-methyl-6H-pyrido[2,3-b][1,4]benzodiazepin-6-one; and, h) 5,11-Dihydro-5,8,11-trimethyl-6H-pyrido[2,3-b][1,4]benzodiazepin-6-one.

Compounds of formula I, wherein Z is oxygen, can be prepared according to the following general methods A through [I] F. Compounds of formula I, wherein Z is sulfur, $=NCN$ or $=NOR^{14}$, can be made according to the following general methods G, H and I.

METHOD A

In this method, which yields a compound of the formula Ia, a compound of the formula II

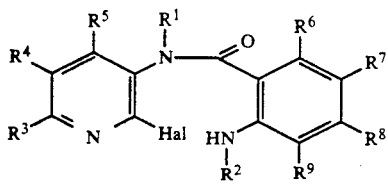

wherein Hal is a halogen atom and $R^1$ through $R^9$ are as set forth above, is cyclized. The cyclisation may be effected by heating the compound of formula II to elevated temperatures, preferably above 150° C., advantageously in the presence of a high-boiling point inert solvent, such as trichlorobenzene, paraffin oil or sulfolane, in the presence of a basic catalyst, such as potash, or copper powder, but preferably in the presence of an acid catalyst such as hydrogen chloride or concentrated sulfuric acid. Upon heating the compound of formula II, the evolution of hydrogen halide begins at temperatures above 150° C., which ceases after heating for several hours. Thereafter, the high-boiling-point solvent which may be present, is distilled off in vacuo, and the desired end product of formula Ia crystallizes when cooling. The raw product is then purified by conventional methods, such as recrystallization from an inert solvent.

METHOD B

In this method, which also yields a compound of the formula Ia, an isatoic acid of the formula III

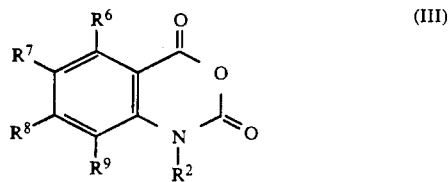

wherein $R^2$ and $R^6$ through $R^9$ are as set forth above, is reacted with a 2-halo-3-aminopyridine of the formula IV

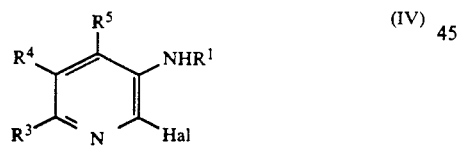

wherein $R^1$ and $R^3$ through $R^5$ are as set forth above and Hal is a halogen atom. The reaction is carried out at a temperature above 150° C. This method makes it possible to prepare a compound of formula Ia with good yields by means of a continuous reaction procedure. The reaction is carried out either without a solvent medium or in the presence of a high-boiling point inert solvent, such as trichlorobenzene, tetraethyleneglycol, tetrahydronaphthalene, sulfolane or the like and preferably in the presence of catalytic amounts of a mineral acid such as hydrogen chloride or concentrated sulfuric acid. Upon heating the reaction mixture, carbon dioxide is initially evolved at temperatures between 120° and 150° C. and a compound of formula II above is formed as an intermediate. However, this intermediate need not be isolated; instead, the intermediate is cyclized in situ, accompanied by evolution of hydrogen halide, by heating the reaction mixture containing it to a temperature above 150° C., preferably to between 180° and 250° C. Of course, the reaction mixture of the compounds of formulas III and IV may also be heated right away to the temperature required for cyclization.

METHOD C

In those instances where methods A or B yield a compound of formula Ia wherein $R^1$ is hydrogen, such compound may, if desired, be converted, using conventional methods, into a compound of formula Ia wherein $R^1$ is other than hydrogen. To accomplish this, a compound of formula Ia, wherein $R^1$ is hydrogen, is first reacted with an alkali metal hydroxide, alkali metal alkoxide, alkali metal amide or alkali metal hydride to form a 5-alkali metal compound as an intermediate. The 5-alkali metal compound thus obtained is then reacted with a compound of the formula $R^1Y$, wherein $R^1$ has the same definitions as set forth above, except for hydrogen, and Y is a leaving group such as chlorine, bromine, iodine, the anion of a reactive ester or the radical of a sulfuric acid ester or of an aliphatic or aromatic sulfonic acid ester.

The preparation of the starting compounds of formula II is described in U.S. Pat. Nos. 3,539,554 and 3,406,168. The starting compounds of formulae III and IV are all known or can be produced in accordance with methods described in the literature.

METHOD D

In Method D, a compound of the formula V

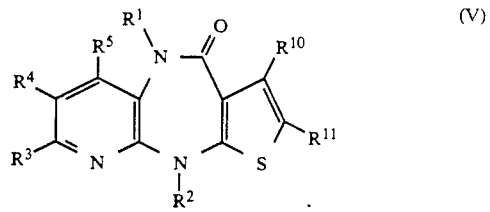

wherein $R^1$ through $R^5$, $R^{10}$, and $R^{11}$ are as defined above, can be prepared from a compound of the formula VI

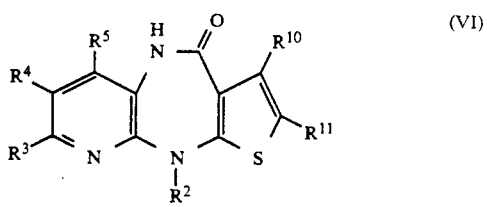

wherein $R^2$ through $R^5$, $R^{10}$ and $R^{11}$ are as defined above, by methods analogous to those described in Method C. A compound of the formula VI can be prepared by cyclization of a compound of the formula VIIa by known per se methods. A compound of formula VIIa can be prepared by known reduction procedures of a nitro compound of formula VIIb.

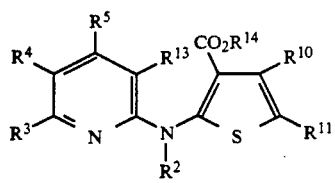 (VII)

A bis-arylamine of formula VIIb can be prepared by condensation of a compound of formula VIII, by known per se methods, with a compound of formula IX, wherein $R^{14}$ is alkyl of 1 to 4 carbon atoms.

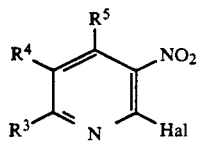 (VIII)

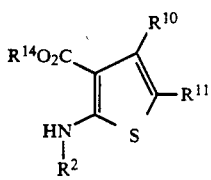 (IX)

Starting materials are known from the literature, may be purchased or may be obtained by procedures known from the literature.

METHOD E

Using Method E, a compound of formula X

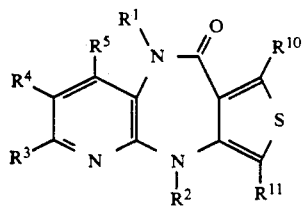 (X)

wherein $R^1$ through $R^5$, $R^{10}$, and $R^{11}$ are as defined above, can be prepared from a compound of the formula XI

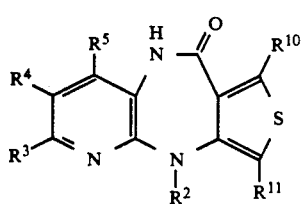 (XI)

wherein $R^2$ through $R^5$, $R^{10}$ and $R^{11}$ are as defined above, by methods analogous to those described in Method C. A compound of the formula XI can be prepared by dehydrogenation of a compound of formula XII by known per se methods.

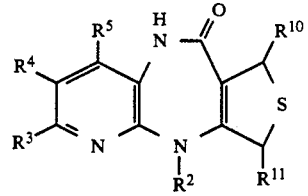 (XII)

A compound of the formula XII can be prepared by known per se methods by condensation of a diaminopyridine of the formula XIII with a tetrahydrothiophene of the formula XIV,

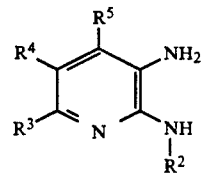 (XIII)

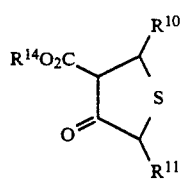 (XIV)

wherein $R^{10}$ and $R^{11}$ are each independently hydrogen or alkyl of 1 to 3 carbon atoms. If desired, a compound of formula XI, wherein one or both of $R^{10}$ and $R^{11}$ are hydrogen, can be halogenated by known per se methods to provide a compound of formula XI wherein one or both of $R^{10}$ and $R^{11}$ are halogen.

Starting materials are known from the literature, may be purchased or may be obtained by procedures known from the literature.

METHOD F

Using Method F, a compound of the formula XV

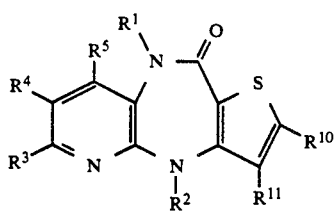 (XV)

wherein $R^1$ through $R^5$, $R^{10}$ and $R^{11}$ are as defined above, can be prepared from a compound of the formula XVI

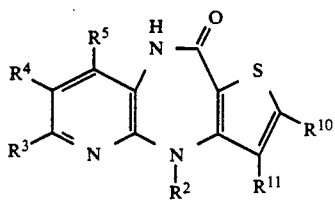 (XVI)

wherein $R^2$ through $R^5$, $R^{10}$ and $R^{11}$ are as defined above, by methods analogous to those described in

11

Method C. A compound of the formula XVI can be prepared by cyclization of a compound of the formula XVIIa by known per se methods. A compound of formula VIIa can be prepared by known reduction procedures of a compound of formula VIIb.

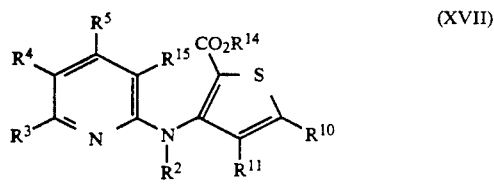

XVIIa: $R^{15}=NH_2$
XVIIb: $R^{15}=NO_2$

A bis-arylamine of formula XVIIb can be prepared by condensation of a compound of formula VIII, by known per se methods, with a compound of formula XVIII, wherein $R^{14}$ is alkyl of 1 to 4 carbon atoms.

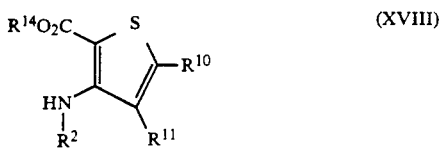

Starting materials are known from the literature, may be purchased or may be obtained by procedures known from the literature.

METHOD G

In Method G, a compound of the formula I, wherein Z is sulfur, is obtained by reacting a compound of the formula I, wherein Z is oxygen, with a sulfurating agent, such as 2,4-bis(4-methoxyphenyl)-1,3-dithia-2,4-diphosphetane-2,4-disulfide; bis(tricyclohexyltin)sulfide; bis(tri-n-butyltin)sulfide; bis(triphenyltin)sulfide; bis(trimethylsilyl)sulfide or phosphorous pentasulfide. The reaction is carried out in an inert organic solvent such as carbon disulfide, benzene or toluene, at room temperature or higher, preferably an elevated temperature up to the boiling point of the reaction mixture, and preferably under anhydrous conditions. When using the above mentioned tin or silyl sulfide, it is preferable to carry out the sulfurization reaction in the presence of a Lewis acid such as boron trichloride.

It will be obvious to those skilled in the art that the presence of another carbonyl moiety in a compound of formula I, for example, a compound wherein Z is oxygen and any of $R^3$ through $R^9$ is alkanoyl, will require that the ketone carbonyl be protected via known methods by a suitable protecting group prior to the sulfurization reaction; deprotection subsequent to the sulfurization reaction provides the desired compound. Similarly, in cases wherein $R^2$ is, for example, alkanoyl, it will be obvious that the sulfurization reaction should be performed prior to the acylation of the 11-position nitrogen. In those cases wherein the substituents at any of $R^3$ through $R^9$ can be derived from nitro, for example, alkanoylamino, the sulfurization reaction can be performed on the corresponding nitro derivative, followed by an appropriate (known) reduction and finally acylation to yield the desired product.

12

METHOD H

Compounds of the formula I, wherein $R^1$ is hydrogen, A and $R^2$ through $R^5$ are as defined above and Z is a group of formula $=NCN$, can be obtained by reacting a compound of the formula XIX

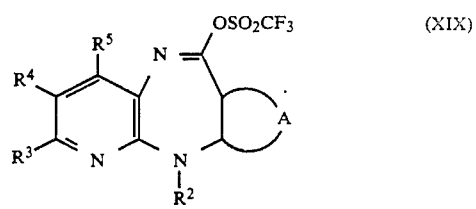

wherein A and $R^2$ through $R^5$ are as defined above, with cyanamide. The reaction is carried out in the presence of a base such as potassium carbonate, sodium carbonate, triethylamine, or diisopropylethylamine, and in an inert solvent such as methylene chloride, 1,4-dioxane, tetrahydrofuran, diethylether, chloroform, or dimethylformamide at a temperature between 0° C. up to the boiling point of the reaction mixture.

METHOD I

Compounds of the formula I, wherein $R^1$ is hydrogen and A and $R^2$ through $R^5$ are as defined above and Z is a group of formula $=NOR^{12}$, can be obtained, in a manner analogous to that of Method H, by reacting a compound of the formula XIX, wherein A and $R^2$ through $R^5$ are as defined above with the appropriate alkoxylamine (O-alkylhydroxylamine) or its salt (for example, methoxylamine hydrochloride). The reaction is carried out under conditions analogous to those described for the treatment of a compound of the formula XIX with cyanamide.

STARTING MATERIALS FOR METHODS H AND I

A compound of the formula XIX wherein A and $R^2$ through $R^5$ are as defined above, can be obtained by reacting a compound of the formula I, wherein $R^1$ is hydrogen and A and $R^2$ through $R^5$ are as defined above and Z is oxygen, with trifluoromethanesulfonic anhydride. The reaction is preferably carried out in an inert solvent using one to two equivalents of trifluoromethanesulfonic anhydride and in the presence of one to two equivalents of a base. The base may be, for example, a tertiary amine such as triethylamine or diisopropyl-ethylamine, and the inert solvent used may include, for example, methylene chloride, chloroform, diethylether, tetrahydrofuran, or toluene. Addition of the reagents is generally carried out at or below ambient temperature, and the mixture is then allowed to react, at or near room temperature.

The alkoxylamine starting material may be purchased, are known from the literature or may be obtained by procedures known from the literature.

As stated before, the compounds provided by the invention inhibit the enzymatic activity of HIV-1 RT. Based upon testing of these compounds, as described below, it is known that they inhibit the RNA-dependent DNA polymerase activity of HIV RT. Based upon other testing, not described herein, it is believed that they also inhibit the DNA-dependent DNA polymerase activity of HIV RT.

Utilizing the Reverse Transcriptase (RT) Assay described below, compounds can be tested for their ability to inhibit the RNA-dependent DNA polymerase activity of HIV RT. Certain specific compounds, described in the Examples which appear below, were so tested. The results of this testing appear in Table I, below.

REVERSE TRANSCRIPTASE (RT) ASSAY

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate.

Materials a) Preparation of the enzyme

Reverse transcriptase enzyme from the LAV strain of Human Immunodeficiency Virus (HIV-1) (1) was isolated from the bacterial strain JM109 (3) expressing the DNA clone pBRTprt1+ (2) which is under the control of the lac promotor in the expression vector pIBI21 (4). An overnight culture grown in 2XYT medium (37° C., 225 rpm) (5) supplemented with 100 μg/ml ampicillin for positive selection is inoculated at a 1:40 dilution into M9 medium supplemented with 10 μg/ml thiamine, 0.5% casamino acids, and 50 μg/ml ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/ml) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2X concentrated stock reaction mixture

| Stock Reagent | 2X Mix Concentration |
| --- | --- |
| 1M Tris pH 7.4 | 100 mM |
| 1M Dithiothrietol | 40 mM |
| 1M NaCl | 120 mM |
| 1% Nonidet P-40 | 0.1% |
| 1M MgCl | 4 mM |
| [poly r(C)/oligo d(G)](5:1) | 2 μg/ml |
| $^3$H-dGTP (81 μM) | 0.6 μM |

Assay Procedure

The 2X concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 μl/well; 3 wells/compound). The HIV-1 RT enzyme is thawed, diluted in 50 mM Tris pH 7.4 so that fifteen μl of diluted enzyme contain 0.001 Unit (one unit is that amount of enzyme to transform 1 micromole of substrate per minute at 25° C.), and fifteen μl are dispensed per well. Twenty μl of 0.12–0.5M EDTA are added to the first three wells of the microtiter plate. EDTA chelates the $Mg^{++}$ present and prevents reverse transcription. This group serves as background polymerization which is subtracted from all other groups. Twenty-five μl of the 2X reaction mixture are added to all wells and the assay is allowed to incubate at room temperature for 60 minutes. The assay is terminated by precipitating the DNA in each well with 50 μl of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mls of scintillation cocktail and is counted in a Beckman beta counter.

The calculation for percent inhibition is as follows:

$$\% \text{ inhibition} = \frac{CPM \text{ Mean Test Value} - CPM \text{ Mean Control Value}}{CPM \text{ Mean Control Value}} \times 100$$

References

1. Benn, S., et al., *Science* 230: 949, 1985.
2. Farmerie, W. G. et. al., *Science* 236: 305, 1987.
3. Yanisch-Perron, C., Viera, J., and Messing, J., *Gene* 33: 103, 1985.
4. International Biotechnologies, Inc., New Haven, Conn. 06535.
5. Maniatis, T, Fritsch, E. F., and J. Sambrook, eds. *Molecular Cloning: A Laboratory Manual*, Cold Spring Harbor Laboratory, 1982.
6. Spira, T., et. al. *J. Clinical Microbiology*, 25: 97, 1987.

In order to confirm that compounds which are active in the RT Assay also have the ability to inhibit HIV replication in a living system, compounds according to the invention were also tested in the human T-Cell Culture Assay described below. The results of this testing appear in Table I.

HUMAN T-CELL CULTURE ASSAY

Assay Theory

Formation of syncytia is a feature of in vitro cultures of CD4+T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method

The target cells, designated c8166, are a subclone of human lymphoma cells of T-cell origin and are established at an initial density of $5 \times 10^4$ per 100 μl in RPMI 1640 (+10% fetal bovine serum) culture medium in 96 well flat bottom plates. A selected amount of test compound, dissolved in DMSO, is included. After 24 hours, 50–100 TCID$_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

References (1) M. Somasundaran and H. L. Robinson, *Science* 242, 1554 (1988).
(2) G. M. Shaw, R. H. Hahn, S. K. Arya, J. E. Groopman, R. C. Gallo and F. Wong-Staal, *Science* 226, 1165 (1984)

In order to assess the specificity of the enzyme inhibitory activity of the compounds provided by the invention, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Cellular Cytotoxicity Assay described below. The results of this testing are reported in Table I, below. Compounds having a relatively high EC$_{50}$ are preferred.

MTT ASSAY FOR CELLULAR CYTOTOXICITY

Assay Theory

The MTT [3-(4,5-dimethylthiazol-2-yl)-2,5 diphenyl tetrazolium bromide] assay is based on cleavage of tetrazolium bromide by metabolically active cells, resulting in a highly quantitative blue color. This assay has been previously described (1) but has been optimized for the purposes of the testing reported herein.

Assay Method

The H9 cell line (2), an established human lymphoma suspension cell line grown in RPMI 1640 supplemented with 10% fetal bovine serum, is used as the target cell line in the assay. Cells (100 μl) are plated in microtest plate wells at a concentration of 10$^5$ cells per ml in the presence of varying concentrations of inhibitor. The cells are incubated at 37° C. in a humidified CO$_2$ incubator. Five days later, 20 μl of MTT (5 mg/ml in RPMI 1640, sonicated, 0.2 micron filtered, and stored at 4° C.) is added to each well. After 4 hours additional incubation at 37° C., 60 μl of Triton-X is added to each well and thoroughly mixed to aid the solubilization of the crystals. Absolute ethanol (5 μl) is added to each well and the resulting mixture is incubated for 30 minutes at 60° C. and immediately read on a plate reader (Dynatech) at a wavelength of 570 nm.

Data from this assay are used to generate a nonlinear regression analysis which yields an EC$_{50}$.

References

1. Mosmann, Tim, *J. Immunol. Methods*, 65: 55, 1983.
2. Jacobs, J. P. *J. Natl. Cancer Inst.*, 34: 231, 1965.

TABLE I

| Compound of Example | RT Inhibition (% @ 10 μg/ml) | T-Cell Culture Assay (% inhibition) | Cytotoxicity Assay (EC$_{50}$) |
|---|---|---|---|
| 1 | 41 | NT | NT |
| 2 | 50 | NT | NT |
| 3 | 87 | NT | NT |
| 4 | 91 | 100% @ 19 μM | 40 μM |
| 5 | 84 | 100% @ 19 μM | NT |
| 6 | 86 | 100% @ 19 μM | NT |
| 7 | 43 | 100% @ 19 μM | NT |
| 8 | 40 | 100% @ 19 μM | NT |
| 9a | 17 | 100% @ 19 μM | NT |
| 9b | 82 | 100% @ 19 μM | NT |
| 9c | 55 | 100% @ 19 μM | NT |
| 9d | 24 | 100% @ 19 μM | NT |
| 9e | 38 | 100% @ 19 μM | NT |
| 9f | 94 | 100% @ 19 μM | NT |
| 9g | 87 | 100% @ 75 μM | 100 μM |
| 9h | 70 | NT | NT |
| 10 | 67 | NT | |

Note: NT = not tested

The following examples further illustrate the present invention and will enable others skilled in the art to understand the invention more completely. It should be understood, however, that the invention is not limited to the particulars given in the examples.

EXAMPLE 1

5-(2-Chloro-2-propenyl)-11-ethyl-5,11-dihydro-6H-pyrido[2,3-b][1,4]benzodiazepin-6-one 9.7 g (0.034 mol) of 5-(2-chloro-2-propenyl)-5,11-dihydro-6H-pyrido[2,3-b][1,4]benzodiazepin-6-one, were suspended in 100 ml of anhydrous dimethylformamide. The mixture was thoroughly purged with dry nitrogen and stirred rapidly while 1.8 g (0.0375 mol) of a 50% dispersion of sodium hydride in mineral oil was slowly added portionwise through an inlet protected by a calcium chloride drying tube. Addition of the first portion sodium hydride resulted in an immediate exothermic reaction, and the temperature of the mixture rose rapidly to about 60° C. After addition of the sodium hydride was complete (30-35 minutes), the reaction mixture was cooled to room temperature, and 7.8 g (0.05 mol) of ethyl iodide were added dropwise. Thereafter, the flask was placed in an oil bath heated to 100° C., and the reaction mixture was stirred and heated for 2 hours, during which time a slow stream of dry nitrogen was passed through the apparatus. After this time no starting material was detected by thin-layer chromatography.

The reaction mixture was cooled to room temperature and, in order to destroy possibly still present sodium hydride, 1 ml of methanol was added. The reaction mixture was evaporated in vacuo, the residue was distributed between 100 ml or ether and 100 ml of water, the organic layer was separated and the aqueous phase was exhaustively extracted with ether. The combined organic layers were dried over sodium sulfate and, after the inorganic salts had been removed by filtration under reduced pressure, the filtrate was evaporated to dryness in vacuo. The highly viscous reddish oil thus obtained was further purified by column chromatography on silica gel (0.2–0.5 mm) using chloroform/ethyl acetate 4/1 (v/v) as an eluent. The crystalline raw material obtained by evaporation of suitable fractions was recrystallized from cyclohexane and from diethyl ether, and yielded 5.9 g (55% of theory) of colorless crystals, having a m.p. of 80°–82° C.

EXAMPLE 2

5,11-Dihydro-2,5,8,11-tetramethyl-6H-pyrido[2,3-b][1,4]benzodiazepin-6-one

Using a procedure analogous to that described in Example 1, the product 5,11-dihydro-2,5,8,11-tetramethyl-6H-pyrido[2,3-b][1,4]benzodiazepin-6-one, m.p. 139°–141° C. (recrystallized from ligroin, b.p. 100°–140° C.) was prepared from 5,11-dihydro-2,5,8-trimethyl-5,11-dihydro-6H-pyrido[2,3-b][1,4]benzodiazepin-6-one and methyl iodide. The yield was 78% of theory.

EXAMPLE 3

5,11-Diethyl-5,11-dihydro-10-methyl-6H-pyrido[2,3-b][1,4]benzodiazepin-6-one

Using a procedure analogous to that described in Example 1, the product 5,11-diethyl-5,11-dihydro-10-methyl-6H-pyrido[2,3-b][1,4]benzodiazepin-6-one, m.p. 143°–144° C. (recrystallized from ligroin, b.p. 100°–140° C.) was prepared from 5-ethyl-10-methyl-5,11-dihydro-6H-pyrido[2,3-b][1,4]benzodiazepin-6-one, m.p. 168°–170° C., and ethyl iodide. The yield was 54% of theory.

EXAMPLE 4

5,11-Dihydro-5,8-Dimethyl-11-ethyl-6H-pyrido[2,3-b][1,4]benzodiazepin-6-one

Using a procedure analogous to that described in Example 1, the product 5,11-dihydro-5,8-dimethyl-11-ethyl-6H-pyrido[2,3-b][1,4]benzodiazepin-6-one, m.p. 137°–138° C. (recrystallized from ligroin, b.p. 100°–140° C.), was prepared from 5,11-dihydro-5,8-dimethyl-6H-pyrido[2,3-b][1,4]benzodiazepin-6-one, and ethyl iodide. The yield was 38% of theory.

EXAMPLE 5

5,11-Dihydro-2,5,10,11-tetramethyl-6H-pyrido[2,3-b][1,4]benzodiazepin-6-one

Using a procedure analogous to that described in Example 1, the product 5,11-dihydro-2,5,10,11-tetramethyl-6H-pyrido[2,3-b][1,4]benzodiazepin-6-one, m.p. 131°–132° C. (recrystallized from ligroin b.p. 100°–140° C.), was prepared from 2,5,10-trimethyl-5,11-dihydro-6H-pyrido[2,3-b][1,4]benzodiazepin-6-one, m.p. 140°–142° C., and methyl iodide. The yield was 28% of theory.

EXAMPLE 6

[5,11-Dihydro-6-oxo-6H-pyrido[2,3-b][1,4]benzodiazepin-11-yl]acetic acid tert-butyl ester A round-bottom flask equipped with a mechanical stirrer, a condenser, a pressure equalizing dropping funnel, a thermometer and a glass joint fitted with a rubber septum was charged with a suspension of 10.5 g (0.05 mol) of 5-11-dihydro-6-oxo-6H-pyrido[2,3-b][1,4]benzo-diazepin-6-one in 550 ml of anhydrous tetrahydrofuran. After cooling to 0° C. with an externally applied ice-salt bath, 96 ml (0.149 mol) of a 1.55 molar solution of n-butyl lithium in hexane was added through the septum by injection from a syringe at a temperature below +10° C. The ice bath was retained for 15 minutes before the mixture was heated to 30°–35° C. to complete the metallation. Thereafter, the mixture was cooled to −10° C., and the solution of 8.0 ml (10.64 g, 0.055 mol) of bromoacetic acid tert-butyl ester in 50 ml of absolute tetrahydrofuran was added dropwise to the stirred mixture. The turbid reaction mixture thus obtained was stirred successively at −10° C. and at room temperature for 2 hours each. The suspension was then stirred into 1 L of brine, and the resulting mixture was exhaustively extracted with ethyl acetate. The combined organic layers were washed with water, dried over anhydrous sodium sulfate and filtered. The solvent was evaporated in vacuo, and the residue was purified by column chromatography on silica gel (0.063–0.2 mm) using dichloromethane/ethyl acetate/cyclohexane 1400/400/50 v/v/v as an eluent. Evaporation of suitable fractions yielded a colorless resin that was identified to be [5,11-dihydro-6-oxo-6H-pyrido[2,3-b][1,4]benzodiazepin-11-yl]acetic acid tert-butyl ester. The yield was 5.6 g (34% of theory).

EXAMPLE 7

2-Chloro-5,11-dihydro-5-ethyl-11-methyl-6H-pyrido[2,3-b][1,4]benzodiazepin-6-one 2-Chloro-5,11-dihydro-11-methyl-6H-pyrido[2,3-b][1,4]benzodiazepin-6-one (64.9 g, 0.25 mol) and 20 g (0.285 mol) of potassium methoxide were mixed with a mixture consisting of 250 ml of absolute dioxan and 250 ml of tertiary butanol, and the mixture was refluxed for two hours. Thereafter, the reaction solution was allowed to cool, 45 g (0.3 mol) of ethyl iodide were then added dropwise over a period of 45 minutes, and the mixture was again refluxed for two hours. Subsequently, the reaction solution was filtered while still hot, the filtrate was evaporated in vacuo, and the residue was recrystallized from cyclohexane. 32.4 g (45% of theory) of 2-chloro-5,11-dihydro-5-ethyl-11-methyl-6H-pyrido[2,3-b][1,4]benzo-diazepin-6-one, m.p. 162°–164° C., were obtained.

EXAMPLE 8

5,11-Dihydro-5,8,11-trimethyl-6H-pyrido[2,3-b][1,4]benzodiazepin-6-one

Using a procedure analogous to that described in Example 1, the product 5,11-dihydro-5,8,11-trimethyl-6H-pyrido[2,3-b][1,4]benzodiazepin-6-one, m.p. 147°–149° C. (recrystallized from ligroin, b.p. 100°–140° C.), was prepared from 5,11-dihydro-5,8-dimethyl-6H-pyrido[2,3-b][1,4]benzodiazepin-6-one, m.p. 176°–178° C., and methyl iodide. The yield was 58% of theory.

EXAMPLE 9

The following known compounds were prepared using the procedures set forth in U.S. Pat. No. 3,539,544:

a) 5,11-Dihydro-11-methyl-6H-pyrido[2,3-b][1,4]benzodiazepin-6-one;

b) 5,11-Dihydro-11-ethyl-6H-pyrido[2,3-b][1,4]benzodiazepin-6-one;

c) 5,11-Dihydro-6H-pyrido[2,3-b][1,4]benzodiazepin-6-one;

d) 5,11-Dihydro-5-ethyl-11-methyl-6H-pyrido[2,3-b][1,4]benzodiazepin-6-one;

e) 5,11-Dihydro-11-methyl-5-n-propyl-6H-pyrido[2,3-b][1,4]benzodiazepin-6-one;

f) 5,11-Dihydro-11-ethyl-5-methyl-6H-pyrido[2,3-b][1,4]-benzodiazepin-6-one;

g) 5,11-Diethyl-5,11-dihydro-6H-pyrido[2,3-b][1,4]benzodiazepin-6-one; and h) 5,11-Dihydro-11-ethyl-5-(2-propenyl)-6H-pyrido[2,3-b][1,4]-benzodiazepin-6-one.

EXAMPLE 10

4,9-Dihydro-9-ethyl-4-methyl-10H-pyrido[3,2-e][1,4]diazepin-10-one a)
4,9-Dihydro-9-ethyl-10H-pyrido[3,2-e][1,4]diazepin-10-one

Add of 2.2 g (0.0917 mol) sodium hydride to a solution of 20.0 g (0.0921 mol) 4,9-dihydro-10H-pyrido[3,2-b]thieno[3,2-e][1,4]diazepin-10-one (prepared as described in Ger. Offen. DE 3,529,372) and subsequently stir until hydrogen is on longer given off. Add dropwise 14.4 g (0.0923 mol) ethyl iodide dissolved in 100 mL dry dimethylformamide over 2 hours and thereafter stir for 2 hours at room temperature. Stir the reaction mixture into 3 L ice water, exhaustively extract with ethyl acetate, dry the ethyl acetate solution over sodium sulfate and concentrate under vacuum. Recrystallize from methanol to give 5.9 g (26% of theory) of a colorless crystal, m.p. 175°–176° C.

b)
4,9-Dihydro-9-ethyl-4-methyl-10H-pyrido[3,2-b]thieno[3,2-e][1,4]diazepin-10-one Dissolve 5.9 g (0.0241 mol) of the compound obtained in step a) in 500 mL anhydrous dimethylformamide and add to the resulting solution, at room temperature, first 0.6 g (0.025 mol) sodium hydride and, after evolution of hydrogen has ceased, 3.4 g (0.024 mol) methyl iodide dropwise. Stir for 2 hours at room temperature and then pour the reaction mixture into 1 L of ice water. Exhaustively extract with ethyl acetate and work up as described in step a). Recrystallize the resulting residue from methanol to yield 2.2 g (35% of theory) of a colorless crystalline product, m.p. 119°–120° C.

EXAMPLE A

Capsules or Tablets

| A-1 | | A-2 | |
|---|---|---|---|
| Ingredients | Quantity | Ingredients | Quantity |
| Compound of Ex. 4 | 250 mg | Compound of Ex. 4 | 50 mg |
| Starch Phosphate | 160 mg | | Dicalcium 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 4 is blended into a powder mixture with the premixed excipient materials as identified above with the exception of the lubricant. The lubricant is then blended in and the resulting blend compressed into tablets or filled into hard gelatin capsules.

EXAMPLE B

Parenteral Solutions

| Ingredients | Quantity |
|---|---|
| Compound of Example 4 | 500 mg |
| Tartaric acid | 1.5 g |
| Benzyl Alcohol | 0.1% by weight |
| Water for injection | q.s. to 100 ml |

The excipient materials are mixed with the water and thereafter the compound of Example 4 is added. Mixing is continued until the solution is clear. The pH of this solution is adjusted to 3.0 and is then filtered into the appropriate vials or ampoules and sterilized by autoclaving.

EXAMPLE C

Nasal Solutions

| Ingredients | Quantity |
|---|---|
| Compound of Example 4 | 100 mg |
| Citric acid | 1.92 g |
| Benzalkonium chloride | 0.025% by weight |
| EDTA | 0.1% of weight |
| Polyvinylalcohol | 10% by weight |
| Water | q.s. to 100 ml |

The excipient materials are mixed with the water and thereafter the compound of Example 4 is added and mixing is continued until the solution is clear. The pH of this solution is adjusted to 4.0 and is then filtered into the appropriate vials or ampoules.

We claim:

1. A method for preventing or treating HIV-1 infection which comprises administering, to a human exposed to or infected by HIV-1, a prophylactically or therapeutically effective amount of a compound of the formula I

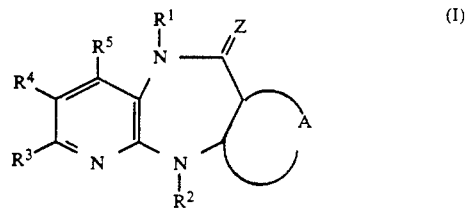

wherein,

A is a fused ring of the formula

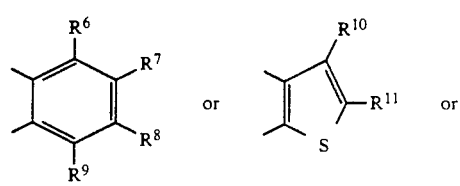

-continued

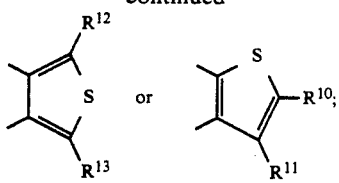

Z is oxygen, sulfur, =NCN or a group of the formula =NOR$^{14}$ wherein R$^{14}$ is alkyl of 1 to 3 carbon atoms;

R$^1$ is hydrogen, alkyl or fluoroalkyl of 1 to 4 carbon atoms, cyclopropyl, alkenyl or alkynyl of 3 to 4 carbon atoms, 2-halo-propen-1-yl, arylmethyl (wherein the aryl moiety is phenyl or thienyl, which is either unsubstituted or substituted by methyl, methoxy or halogen), acetyl, or alkoxyalkyl or alkylthioalkyl of 2 to 3 carbon atoms;

R$^2$ is alkyl or fluoroalkyl of 1 to 4 carbon atoms, cycloalkyl of 3 to 5 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl, thienyl or furanyl, which is either unsubstituted or substituted by alkyl or alkoxy of 1 to 3 carbon atoms, hydroxyl or halogen), phenyl (which is either unsubstituted or substituted by alkyl or alkoxy of 1 to 3 carbon atoms, halogen or hydroxyl) or alkoxycarbonylmethyl wherein the alkoxy moiety contains 1 to 5 carbon atoms;

R$^3$, R$^4$ and R$^5$ are each independently hydrogen, alkyl of 1 to 3 carbon atoms or chloro, with the proviso that at least one of these substituents is hydrogen or methyl; or, one of R$^3$, R$^4$ and R$^5$ is butyl, alkanoyl of 2 to 4 carbon atoms, alkoxycarbonyl or 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, aryl or arylalkyl (wherein the alkyl moiety contains 1 to 3 carbon atoms, and the aryl moiety is phenyl, thienyl, furanyl, pyridyl, or imidazolyl, which is either unsubstituted or substituted by alkyl or alkoxy of 1 to 3 carbon atoms, hydroxyl or halogen), alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 3 carbon atoms, N-pyrrolidino, N-piperidino, N-morpholino, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, with the proviso that the remaining two substituents are hydrogen or methyl; or, when Z is oxygen, one of R$^3$, R$^4$ and R$^5$ is alkylsulfinyl or alkylsulfonyl of 1 to 3 carbon atoms, with the proviso that the remaining two substituents are hydrogen or methyl;

R$^6$, R$^7$, R$^8$ and R$^9$ are each hydrogen; or one of R$^6$, R$^7$, R$^8$ and R$^9$ is alkyl of 1 to 4 carbon atoms, alkanoyl of 2 to 4 carbon atoms, alkoxycarbonyl of 2 to 4 carbon atoms, hydroxyalkyl of 1 to 4 carbon atoms, alkoxycarbonylalkyl wherein the alkoxy and alkyl moieties each contain 1 to 2 carbon atoms, halogen, trihalomethyl, hydroxyl, alkoxy of 1 to 3 carbon atoms, alkylthio of 1 to 3 carbon atoms, alkanoyloxy of 2 to 3 carbon atoms, alkanoylamino of 1 to 3 carbon atoms, aminoalkyl of 1 to 3 carbon atoms, mono- or di-alkylamino wherein each alkyl moiety contains 1 to 2 carbon atoms, carboxyalkyl of 2 to 3 carbon atoms, cyano, nitro, carboxyl, carbamyl, amino, azido, mono- or di-alkylaminoalkyl wherein each alkyl moiety contains 1 to 2 carbon atoms, and the remaining three substituents are hydrogen or two of the remaining three substituents are hydrogen and one is methyl, ethyl or halogen;

R$^{10}$ and R$^{11}$ are each independently hydrogen, alkyl of 1 to 3 carbon atoms or halogen; and, R$^{12}$ and R$^{13}$ are each independently hydrogen, methyl, ethyl or halogen, or a pharmaceutically acceptable acid addition salt thereof.

2. The method of claim 1, utilizing a compound of the formula Ia,

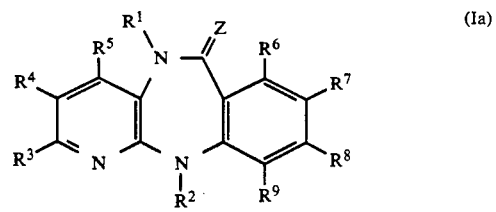

wherein,

Z is oxygen or sulfur;

R$^1$ is hydrogen, alkyl of 1 to 3 carbon atoms, allyl, propargyl, 2-halo-propen-1-yl, methoxymethyl or methylthiomethyl;

R$^2$ is alkyl 1 to 4 carbon atoms, cycloalkyl of 3 to 4 carbon atoms, alkenyl or alkynyl of 2 to 4 carbon atoms, alkoxyalkyl or alkylthioalkyl of 2 to 3 carbon atoms, alkanoyl of 2 to 3 carbon atoms, hydroxyalkyl of 2 to 4 carbon atoms, arylmethyl (wherein the aryl moiety is phenyl or thienyl, which is either unsubstituted or substituted by methyl, methoxy or halogen) or alkoxycarbonylmethyl wherein the alkoxy moiety contains 1 to 4 carbon atoms;

R$^3$, R$^4$, and R$^5$ are each independently hydrogen, methyl, chloro, mono- or di-alkylamino wherein each alkyl moiety contains 1 to 3 carbon atoms, N-pyrrolidino, N-piperidino or N-morpholino, with the proviso that at least one of these substituents is hydrogen or methyl, or R$^5$ is ethyl, propyl or butyl with the remaining two substituents being hydrogen;

R$^6$ is hydrogen, or methyl or ethyl with the proviso that R$^7$ is hydrogen or methyl;

R$^7$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyloxy, alkanoylamino of 1 to 2 carbon atoms or cyano, with the proviso that R$^8$ is hydrogen;

R$^8$ is alkyl of 1 to 2 carbon atoms, acetyl, hydroxyalkyl of 1 to 2 carbon atoms, alkoxycarbonyl of 2 to 3 carbon atoms, alkoxycarbonylalkyl wherein the alkoxy and alkyl moieties each contain 1 to 2 carbon atoms, halogen, trifluoromethyl, hydroxyl, alkoxy of 1 to 2 carbon atoms, alkylthio of 1 to 2 carbon atoms, acetyl, alkanoylamino of 1 to 2 carbon atoms or cyano, with the proviso that $R^7$ is hydrogen; or, $R^7$ and $R^8$ are both hydrogen, methyl or halogen; and, $R^9$ is hydrogen, or methyl with the proviso that $R^8$ is hydrogen or methyl;

or a pharmaceutically acceptable acid addition salt thereof.

3. The method of claim 2, wherein, in the compound of formula Ia:
Z is oxygen or sulfur;
$R^1$ is hydrogen, 2-halo-2-propen-1-yl, or alkyl of 1 to 3 carbon atoms;
$R^2$ is alkyl of 1 to 4 carbon atoms or cycloalkyl of 3 to 4 carbon atoms;
$R^3$ is hydrogen, methyl, chloro, methoxy, mono- or di-alkylamino wherein each alkyl moiety contains 1 to 3 carbon atoms, or N-pyrrolidino;
$R^4$ and $R^5$ are each independently hydrogen or methyl; and,
$R^6$ through $R^9$ are each hydrogen.

* * * * *